(12) United States Patent
Manweiler et al.

(10) Patent No.: US 10,198,773 B2
(45) Date of Patent: Feb. 5, 2019

(54) COOPERATIVE EVIDENCE GATHERING

(71) Applicant: International Business Machines Corporation, Armonk, NY (US)

(72) Inventors: Justin G. Manweiler, Somers, NY (US); Jan S. Rellermeyer, Austin, TX (US); Eric J. Rozner, Austin, TX (US); James Xenidis, Cedar Park, TX (US)

(73) Assignee: International Business Machines Corporation, Armonk, NY (US)

( * ) Notice: Subject to any disclaimer, the term of this patent is extended or adjusted under 35 U.S.C. 154(b) by 515 days.

(21) Appl. No.: 14/852,000

(22) Filed: Sep. 11, 2015

(65) Prior Publication Data

US 2017/0076394 A1   Mar. 16, 2017

(51) Int. Cl.
| | | |
|---|---|---|
| *G06Q 40/00* | (2012.01) | |
| *G06Q 40/08* | (2012.01) | |
| *G06F 19/00* | (2018.01) | |
| *G07C 5/08* | (2006.01) | |
| *G07C 5/00* | (2006.01) | |

(52) U.S. Cl.
CPC ........... *G06Q 40/08* (2013.01); *G06F 19/328* (2013.01); *G07C 5/085* (2013.01); *G07C 5/008* (2013.01)

(58) Field of Classification Search
CPC ...... B60Q 1/2665; B60Q 3/258; B60Q 5/006; G06Q 30/0645; G06Q 40/08; G06K 9/00832
See application file for complete search history.

(56) References Cited

U.S. PATENT DOCUMENTS

| | | | |
|---|---|---|---|
| 6,141,611 A | 10/2000 | Mackey et al. | |
| 6,570,609 B1 | 5/2003 | Heien | |
| 6,738,088 B1 | 5/2004 | Uskolovsky et al. | |
| 6,778,818 B1 | 8/2004 | O'Neil | |
| 8,135,510 B2 | 3/2012 | Nakamura | |
| 9,240,082 B2 | 1/2016 | Marathe | |
| 2002/0145666 A1* | 10/2002 | Scaman | B60R 11/04 348/148 |
| 2003/0090568 A1 | 5/2003 | Pico | |
| 2004/0027255 A1* | 2/2004 | Greenbaum | G07C 5/008 340/945 |
| 2011/0154118 A1 | 6/2011 | Tran | |

(Continued)

FOREIGN PATENT DOCUMENTS

CN           203193723 U        9/2013

OTHER PUBLICATIONS

U.S. Appl. No. 15/010,763, filed Jan. 29, 2016.

(Continued)

*Primary Examiner* — Kirsten S Apple
*Assistant Examiner* — Mike Anderson
(74) *Attorney, Agent, or Firm* — Christopher K. McLane; Maeve M. Carpenter

(57) ABSTRACT

In an approach to cooperative evidence gathering, a first computing device receives a request for data corresponding to an event, where a second computing device detecting the event initiates the request for data. The first computing device aggregates data from one or more sensors, the one or more sensors associated with one or more first computing devices within a proximity of a location of the event. The first computing device determines whether at least a portion of the aggregated data is applicable to the event.

10 Claims, 5 Drawing Sheets

(56) References Cited

U.S. PATENT DOCUMENTS

| | | |
|---|---|---|
| 2011/0273568 A1 | 11/2011 | Lagassey |
| 2012/0215446 A1 | 8/2012 | Schunder |
| 2013/0036117 A1* | 2/2013 | Fisher ............... G06F 17/30029 707/736 |
| 2013/0151202 A1 | 6/2013 | Denny et al. |
| 2013/0273877 A1 | 10/2013 | Kote et al. |
| 2014/0009275 A1 | 1/2014 | Bowers et al. |
| 2014/0277902 A1* | 9/2014 | Koch ..................... G07C 5/008 701/29.1 |
| 2015/0142881 A1* | 5/2015 | Kalaboukis ......... G06F 21/6245 709/203 |
| 2015/0161877 A1 | 6/2015 | Hamalainen et al. |
| 2015/0327039 A1* | 11/2015 | Jain ........................ H04W 4/90 455/404.2 |

OTHER PUBLICATIONS

List of IBM Patents or Patent Applications Treated as Related (Appendix P), filed herewith.

Agarwal et al., "Building Rome in a Day", International Conference on Computer Vision, 2009, Kyoto, Japan, printer on: Jun. 1, 2015, 8 pages, <http://grail.cs.washington.edu/rome/>.

Agarwal et al., "Building Rome in a Day", Communications of the ACM, vol. 54, No. 10, Oct. 2011, pp. 105-112, © 2011, ACM, <http://grail.cs.washington.edu/rome/>.

Agarwal et al., "Reconstructing Rome", IEEE Computer Society, Jun. 2010, © 2010, IEEE, pp. 40-47, <http://grail.cs.washington.edu/rome/>.

Aldunate et al., "Early Vehicle Accident Detection and Notification Based on Smartphone Technology", in G. Urzaiz et al. (Eds.): UCAmI 2013, Dec. 2-6, 2013, "Ubiquitous Computing and Ambient Intelligence", Context-Awareness and Context-Driven Interaction Lecture Notes in Computer Science, vol. 8276, pp. 358-365, © Springer International Publishing, Switzerland, 2013, <http://rd.springer.com/chapter/10.1007%2F978-3-319-03176-7_46>.

Bao et al., "MoVi: Mobile Phone based Video Highlights via Collaborative Sensing", MobiSys'10, Jun. 15-18, 2010, San Francisco, California, USA, Copyright 2010, ACM, 14 pages, <http://synrg.csl.illinois.edu/papers/MoVi.pdf>.

Chinna Rao et al., "Accident Detection in Vehicular Networks Using Android-based Smartphones", International Journal of Scientific Research in Computer Science (IJSRCS), vol. 2, Issue 1, Jan. 2014, pp. 24-26.

Copeland, "Fatal hit-and-run crashes on rise in U.S.", USA Today; Nov. 10, 2013, pp. 1-3, <http://www.usatoday.com/story/news/nation/2013/11/10/hit-and-run-crashes-los-angeles/3452699/>.

Fitchard, "IBM to start crunching connected car data for Peugeot", Gigaom; Mar. 25, 2014, pp. 1-4, <https://gigaom.com/2014/03/25/ibm-to-start-crunching-connected-car-data-for-peugeot/>.

Jain et al., "FOCUS: Clustering Crowdsourced Videos by Line-of-Sight", SenSys '13, Nov. 11-15, 2013, Roma, Italy, Copyright 2013, ACM, 14 pages, <http://synrg.csl.illinois.edu/papers/focus-sensys.pdf>.

Simoens et al., "Scalable Crowd-Sourcing of Video from Mobile Devices", MobiSys'13, Jun. 25-28, 2013, Taipei, Taiwan, Copyright 2013, ACM, 14 pages, <http://users.atlantis.ugent.be psimoens/2013_MobiSys_ScalableCrowdSourcingOfVideoFromMobileDevices.pdf>.

Thompson et al., "Using Smartphones to Detect Car Accidents and Provide Situational Awareness to Emergency Responders", Jun. 30-Jul. 2, 2010, 14 pages, <https://www.dre.vanderbilt.edu/~schmidt/PDF/wreckwatch.pdf>.

White et al., "WreckWatch: Automatic Traffic Accident Detection and Notification with Smartphones", Mar. 22, 2011, Journal of Mobile Networks and Applications manuscript No., pp. 1-28, <https://www.dre.vanderbilt.edu/~schmidt/PDF/wreckwatchj.pdf>.

"Collective Vehicular Sensing Incorporating a Vehicle's Operational Data as Indirect Sensors", An IP.com Prior Art Database Technical Disclosure, IP.com No. 000216685, IP.com Electronic Publication: Apr. 13, 2012, pp. 1-2.

* cited by examiner

COOPERATIVE EVIDENCE GATHERING

BACKGROUND OF THE INVENTION

The present invention relates generally to the field of data processing, and more particularly to cooperative evidence gathering in response to an event.

In the current state of transportation technology, most recent generation vehicles come equipped with a range of sensing capabilities and other operational information that systems can treat as indirect sensors. The sensors can help in identifying a variety of issues regarding transportation such as weather and road conditions, as well as documenting conditions of the vehicle and its surroundings.

Crowdsourcing can be defined as the process of obtaining needed services, ideas, or content by soliciting contributions from a large group of people, and especially from an online community. Crowdsourcing often consists of a person or entity broadcasting a problem to the public and an open call for contributions to solving the problem. Members of the public submit solutions which are then owned by the entity which broadcasted the problem.

SUMMARY

Embodiments of the present invention disclose a method, a computer program product, and a system for cooperative evidence gathering. The method may include a first computing device receiving a request for data corresponding to an event, where a second computing device detecting the event initiates the request for data. The first computing device aggregates data from one or more sensors, the one or more sensors associated with one or more first computing devices within a proximity of a location of the event. The first computing device determines whether at least a portion of the aggregated data is applicable to the event.

DETAILED DESCRIPTION

Traffic accidents often occur quickly and with no warning. Hit-and-run accidents are known to be increasing in frequency in many major cities, often resulting in fatalities. Drivers are more likely to flee the scene of the accident if they feel there is a reason to avoid interacting with authorities, such as having a high blood-alcohol content or driving without a proper license. Finding evidence of the cause of an accident, especially a hit-and-run accident, can be crucial to determining the person at fault as well as processing insurance claims. Embodiments of the present invention recognize that improvements can be made to accident reporting by crowdsourcing an evidence request from both stationary and mobile witness devices to an accident. Implementation of embodiments of the invention may take a variety of forms, and exemplary implementation details are discussed subsequently with reference to the Figures.

Figure 1:
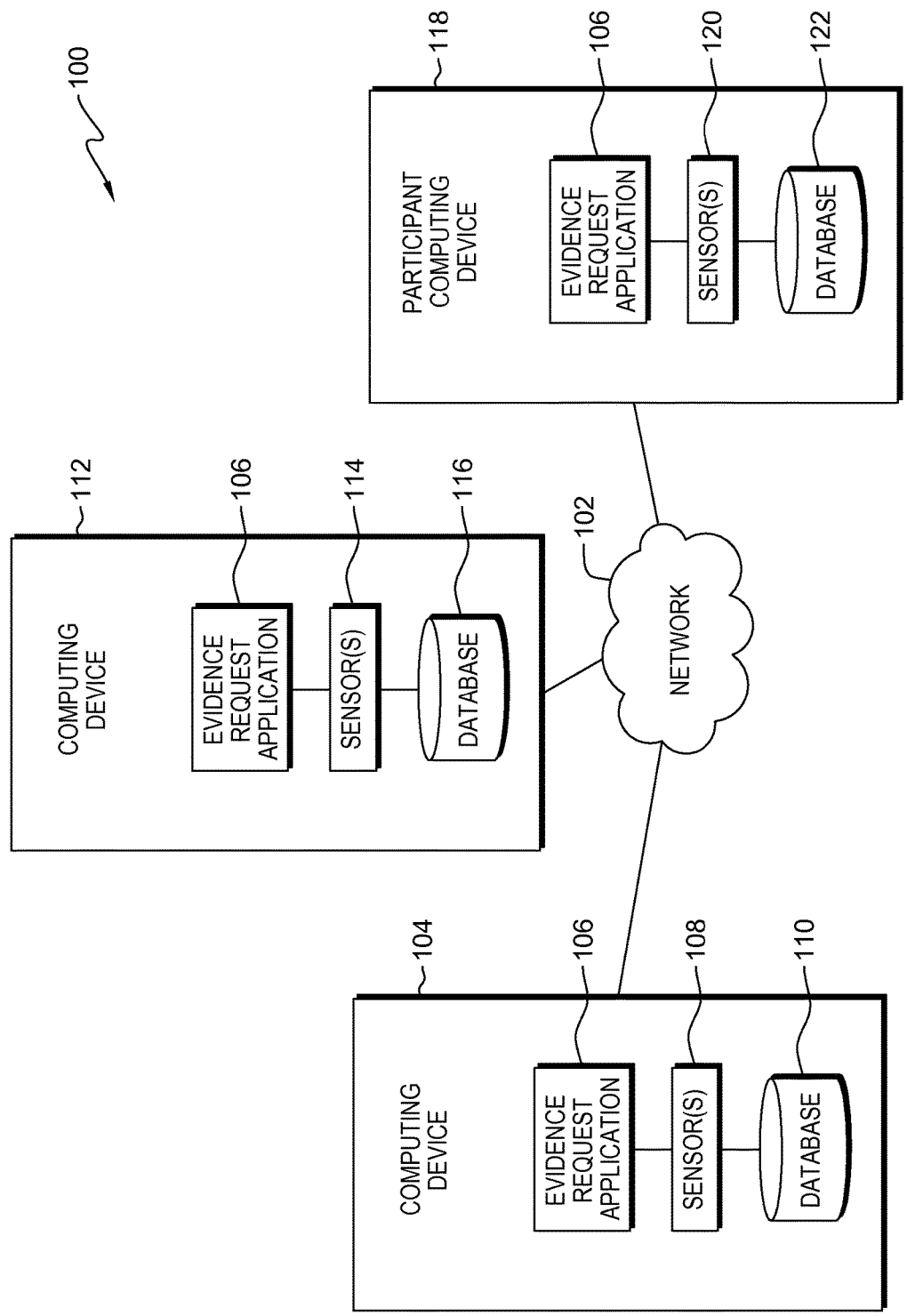
FIG. 1 is a functional block diagram illustrating a distributed data processing environment, in accordance with an embodiment of the present invention.

FIG. 1 is a functional block diagram illustrating a distributed data processing environment, generally designated 100, in accordance with one embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes computing device 104, computing device 112, and participant computing device 118, all interconnected over network 102. Network 102 can be, for example, a telecommunications network, a local area network (LAN), a wide area network (WAN), such as the Internet, or a combination of the three, and can include wired, wireless, or fiber optic connections. Network 102 can include one or more wired and/or wireless networks that are capable of receiving and transmitting data, voice, and/or video signals, including multimedia signals that include voice, data, and video information. In general, network 102 can be any combination of connections and protocols that will support communications between computing device 104, computing device 112, and participant computing device 118, and other computing devices (not shown) within distributed data processing environment 100.

Computing device 104 and computing device 112 each represent one or more computing devices with which participant computing device 118 communicates, via network 102. Participant computing device 118 is a device that is a participant in an event, such as a traffic accident, a collision, a crash, a robbery, etc., while computing device 104 and computing device 112 can act as witnesses to the event. Computing device 104, computing device 112, and participant computing device 118 can each be a laptop computer, a tablet computer, a smart phone, a computer integrated in a vehicle, a computer integrated in a traffic monitoring system, or any programmable electronic device capable of communicating with various components and devices within distributed data processing environment 100, via network 102. In general, computing device 104, computing device 112, and participant computing device 118 each represent any programmable electronic device or combination of programmable electronic devices capable of executing machine readable program instructions and communicating with other computing devices (not shown) within distributed data processing environment 100 via a network, such as network 102. Computing device 104, computing device 112, and participant computing device 118 each include evidence request application 106. Computing device 104 also includes sensor(s) 108 and database 110. Computing device 112 also includes sensor(s) 114 and database 116. Participant computing device 118 also includes sensor(s) 120 and database 122.

Evidence request application 106 enables an associated device, such as participant computing device 118, to initiate cooperative evidence gathering by broadcasting a request for evidence to other devices proximately located with participant computing device 118 during a detected event, such as a traffic accident or a robbery. As referred to herein, proximately located is defined as devices within a distance, or proximity, to participant computing device 118 during a detected event to be able to receive the broadcasted request by one or more communication techniques, including wired and wireless techniques, and within a distance that one or more sensors associated with the devices receiving the request can sense conditions associated with the event or the location of the event. For example, if participant computing device 118 is a mobile phone, then a device within cellular network range of participant computing device 118 that includes one or more sensors that can view or hear the event or monitor weather conditions in the location of the event are proximately located with participant computing device 118. Evidence request application 106 on devices proximately located with participant computing device 118, such as computing device 104 and computing device 112, receives the broadcasted request and activates any relevant, associated sensors that are not already activated. Evidence request application 106 aggregates, i.e., collects and combines, data generated by associated sensors and determines whether at least a portion of the aggregated data is applicable to the evidence request. Evidence request application 106 may also include one or more policies with which evidence request application 106 determines whether data transmission is allowed. Evidence request application 106 may include a logic engine that can coordinate policies and determine if evidence is applicable. If applicable and allowed, evidence request application 106 transmits data to the broadcasting device or to another entity. Evidence request application 106 may include a history manager that keeps relevant history and can aid in responding to an evidence request. By enabling crowdsourcing of evidence, evidence request application 106 quickly and efficiently aggregates evidence of an event from a plurality of vantage points before the sources of the evidence can be lost. In the depicted embodiment, evidence request application 106 resides on each of the computing devices. In another embodiment, evidence request application 106 can reside on a central server computer (not shown) that receives an event detection, broadcasts a request for data, and receives data transmission through a user interface that resides on each computing device. In the embodiment, computing devices and the associated sensors can be pre-registered with evidence request application 106 regarding sensor type, location, vantage point, hours of operation, etc., and evidence request application 106 can broadcast a request for evidence to specific devices, as needed. Evidence request application 106 is depicted and described in further detail with respect to FIG. 2, FIG. 3, and FIG. 4.

Sensor(s) 108, sensor(s) 114, and sensor(s) 120 are each one or more of a plurality of sensors associated with computing device 104, computing device 112, and participant computing device 118, respectively. In the depicted embodiment, sensor(s) 108, sensor(s) 114, and sensor(s) 120 reside on computing device 104, computing device 112, and participant computing device 118, respectively. In another embodiment, sensor(s) 108, sensor(s) 114, and sensor(s) 120 are proximately located with computing device 104, computing device 112, and participant computing device 118, respectively. Sensor(s) 108, sensor(s) 114, and sensor(s) 120 may be one or more transducers whose purpose is to sense, i.e., to detect, some characteristic of its environment. A transducer sensor, such as sensor(s) 108, sensor(s) 114, and sensor(s) 120, detects events or changes in quantities and provides a corresponding output, generally as an electrical or optical signal. For example, a thermocouple converts temperature to an output voltage. Sensor(s) 108, sensor(s) 114, and sensor(s) 120 may also be one or more cameras, microphones, or other recording devices that can capture evidence of an event. Sensor(s) 108, sensor(s) 114, and sensor(s) 120 generate data that may be applicable or relevant to an evidence request made by evidence request application 106.

In the depicted embodiment, database 110, database 116, and database 122 reside on computing device 104, computing device 112, and participant computing device 118, respectively. In another embodiment, database 110, database 116, and database 122 reside on a centralized computing device in distributed data processing environment 100 (not shown). A database is an organized collection of data. Database 110, database 116, and database 122 can each be implemented with any type of storage device capable of storing data and configuration files that can be accessed and utilized by computing device 104, computing device 112, and participant computing device 118, respectively, such as a database server, a hard disk drive, or a flash memory. If directed by evidence request application 106, then database 110, database 116, and database 122 each stores data generated by sensor(s) 108, sensor(s) 114, and sensor(s) 120, respectively, in response to an event. Database 110, database 116, and database 122 may each store data generated by sensor(s) 108, sensor(s) 114, and sensor(s) 120, respectively, while the sensors are active, whether or not an event triggers the activation of the sensors. Database 110, database 116, and database 122 may also store policies associated with computing device 104, computing device 112, and participant computing device 118, respectively, that evidence request application 106 uses to determine whether data generated by sensor(s) 108, sensor(s) 114, and sensor(s) 120 in response to an event are applicable to a request for evidence.

Figure 2:
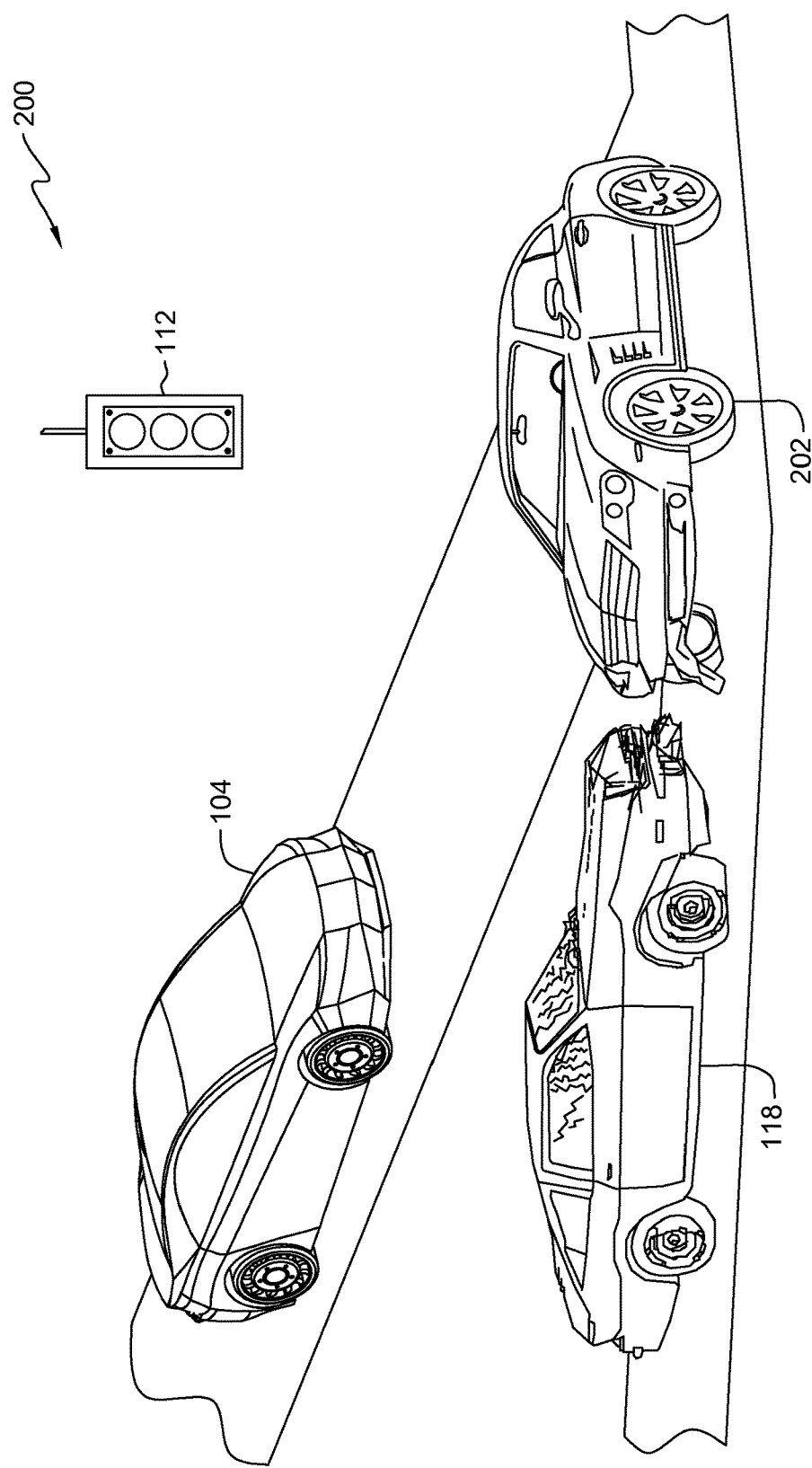
FIG. 2 depicts an example of a scenario where an evidence request application is applied.

FIG. 2 depicts an example of a scenario where evidence request application 106 is applied. In diagram 200, computing device 104 resides in a car and sensor(s) 108 are associated with the car. Examples of sensor(s) 108 in the depicted environment can include, but are not limited to, a speedometer, a rear-view camera, and a global positioning system (GPS) device. Computing device 104 is an example of a non-stationary device, for example, a smart phone in the car or a computing device integrated with the car itself. Also in diagram 200, computing device 112 resides on a stop light and sensor(s) 114 are associated with the stop light. Examples of sensor(s) 114 include, but are not limited to, a traffic monitoring camera and a microphone. Computing device 112 is an example of a stationary device. Diagram 200 depicts participant computing device 118 residing in a car, and participant computing device 118 may be a device such as a smart phone in the car or a computing device integrated with the car itself. In the example, the car associated with participant computing device 118 is involved in an accident with car 202. As a result of detecting the collision, evidence request application 106 on participant computing device 118 broadcasts a request for data that can be used as evidence. Evidence request application 106 on computing device 104 receives the request for data, but determines data generated by sensor(s) 108, for example, a rear-view camera, is not applicable since the accident occurred in a direction opposite the rear-view camera.

Evidence request application 106 on computing device 112 also receives the request for data, and determines data generated by sensor(s) 114 is applicable since the traffic monitoring camera photographed the accident. Evidence request application 106 on computing device 112 can transmit one or more photographs, or other sensor data, and associated metadata to participant computing device 118.

Figure 3:
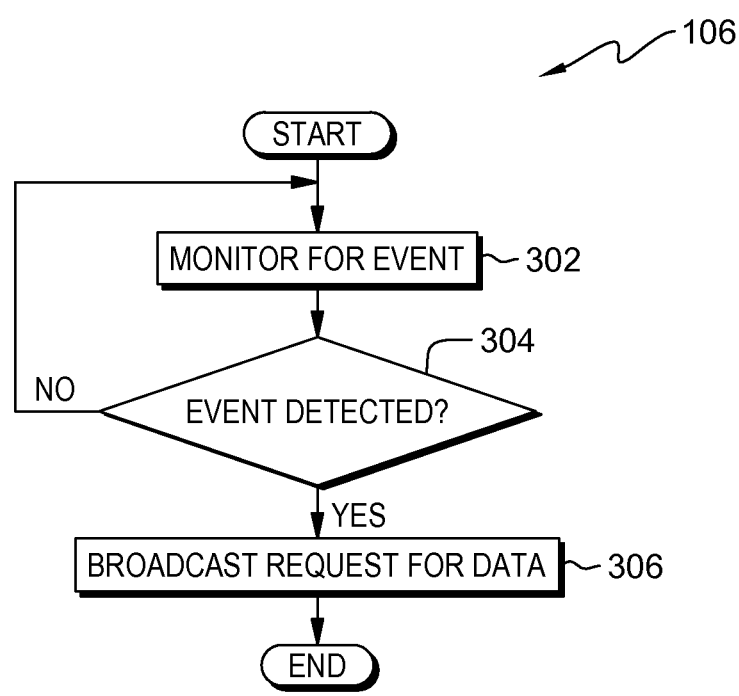
FIG. 3 is a flowchart depicting operational steps of the evidence request application, on a participant computing device within the distributed data processing environment of FIG. 1, for requesting evidence, in accordance with an embodiment of the present invention.

FIG. 3 is a flowchart depicting operational steps of evidence request application 106, on participant computing device 118 within distributed data processing environment 100 of FIG. 1, for requesting evidence, in accordance with an embodiment of the present invention.

Evidence request application 106 monitors for an event (step 302). As will be recognized by one skilled in the art, there exist a plurality of techniques to monitor for an event. For example, sensors embedded in cars and trucks can detect a collision, and, for example, deploy an airbag when a collision is detected. Evidence request application 106 on participant computing device 118 monitors sensor(s) 120 for the occurrence of an event.

Evidence request application 106 determines whether an event is detected (decision block 304). While monitoring sensor(s) 120, evidence request application 106 determines whether sensor(s) 120 detect an event, such as a collision. If evidence request application 106 determines an event is not detected ("no" branch, decision block 304), then evidence request application 106 returns to step 302 to continue monitoring for an event.

If evidence request application 106 determines an event is detected ("yes" branch, decision block 304), then evidence request application 106 broadcasts a request for data (step 306). In one embodiment, evidence request application 106 broadcasts a request for data to a central service that resides on a server computer within distributed data processing environment 100 (not shown) via network 102. In response to receiving the request for data, the central service forwards the request to computing devices proximately located with participant computing device 118. In another embodiment, evidence request application 106 broadcasts a request for data directly to nearby computing devices that include evidence request application 106 via one of a plurality of wired or wireless communication technologies, as are known in the art. The request for data may include a list of specific information that will be useful to the sender of the request, authorities, first responders, health care providers, insurance companies, etc. For example, the request may include questions such as: What evidence do you have from <time, date>?; Can you provide metadata from an event that occurred on the fifth of June?; Were you at a specific intersection ten minutes prior to an accident?; Are you willing to testify in court? In another example, the request for data may include a request for all photographs taken in a specific direction at a specific time. In yet another example, the request for data may ask for evidence that windshield wipers were active at the time of an accident. The request for data may also include information to help determine the applicability of any collected evidence, such as the location of the event, the time the event occurred, other geo-temporal points of interest, a description of a party involved in the event, and sample evidence. The request for data may include instructions as to where to send the data.

Figure 4:
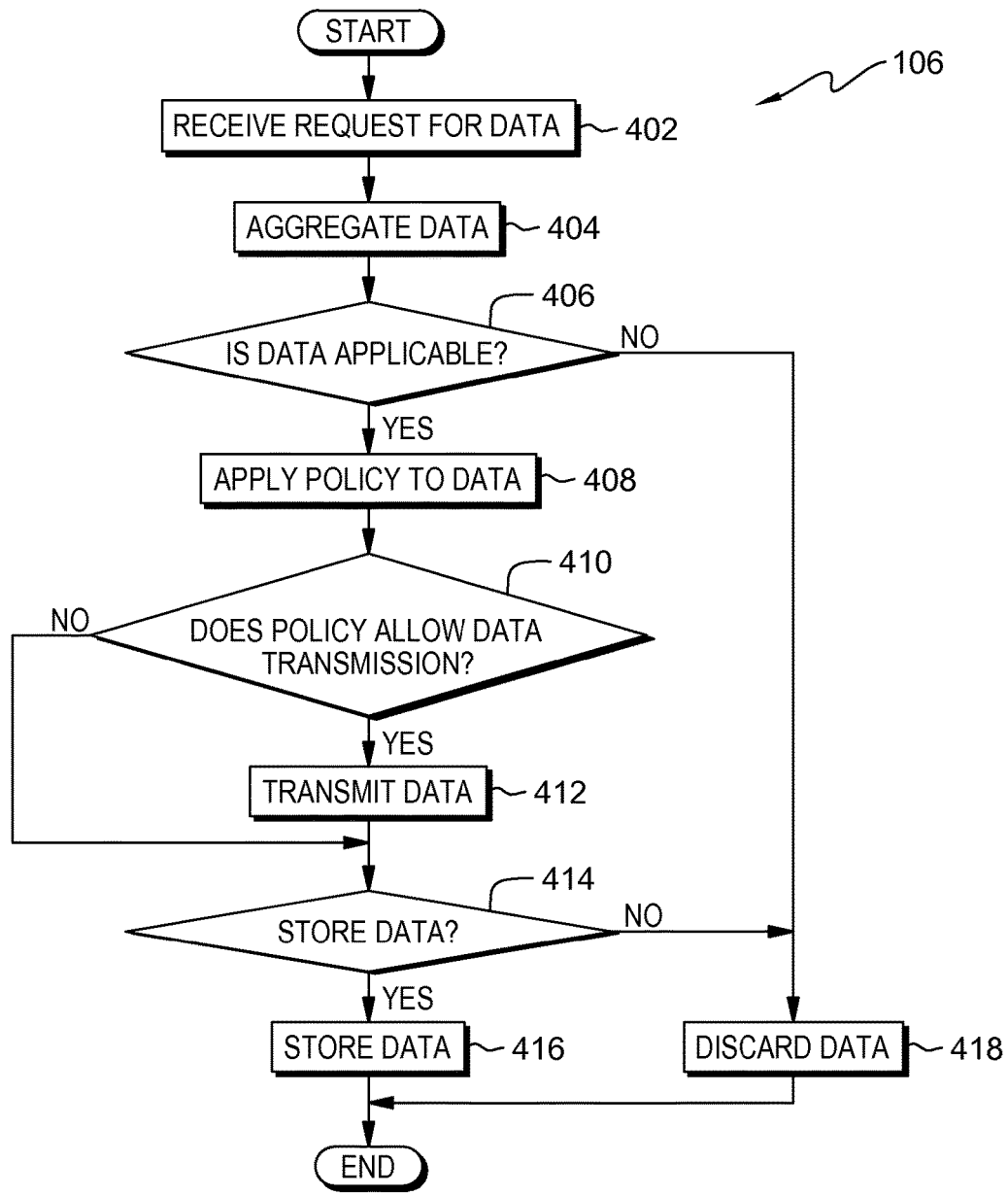
FIG. 4 is a flowchart depicting operational steps of the evidence request application, on one or more computing devices within the distributed data processing environment of FIG. 1, for sharing evidence, in accordance with an embodiment of the present invention.

FIG. 4 is a flowchart depicting operational steps of evidence request application 106, on computing device 104 and/or computing device 112 within distributed data processing environment 100 of FIG. 1, for sharing evidence, in accordance with an embodiment of the present invention.

Evidence request application 106 receives a request for data (step 402). When participant computing device 118 broadcasts a request for data, as described with respect to step 306 of FIG. 3, evidence request application 106 residing on computing devices proximately located with participant computing device 118, such as computing device 104 and computing device 112, receives the request for data which may be used as evidence to an event in which participant computing device 118 is a participant. As described with respect to FIG. 3, evidence request application 106 may receive the request directly from participant computing device 118 or from a centralized service.

Evidence request application 106 aggregates data (step 404). Aggregating, as referenced herein, refers to collecting and combining the data generated by one or more sensors which may include associated metadata. Receipt of a request for data automatically triggers evidence request application 106 to aggregate data generated by one or more sensors associated with the computing device, such as sensor(s) 108 associated with computing device 104. If sensor(s) 108 are actively generating data at the time evidence request application 106 receives the request for data, then evidence request application 106 aggregates data, generated during the time frame of the data request, from sensor(s) 108. For example, if sensor(s) 108 include a GPS, then evidence request application 106 aggregates location data from the time of the data request. If sensor(s) 108 are not actively generating data at the time evidence request application 106 receives the request for data, then evidence request application 106 triggers sensors(s) 108 to activate and begin generating data. For example, if sensor(s) 108 includes a rear-view camera that was not on at the time evidence request application 106 received the data request, then evidence request application 106 triggers the rear-view camera to turn on and begin recording. In one embodiment, evidence request application 106 aggregates metadata associated with generated data. For example, if sensor(s) 108 includes a microphone, evidence request application 106 aggregates the sound recording as well as the time and location in which the microphone recorded the sound.

Evidence request application 106 determines whether the aggregated data is applicable (decision block 406). Although computing device 104 and computing device 112 are proximately located with participant computing device 118 and to the event that occurred, the data that evidence request application 106 aggregates from sensors associated with computing device 104 and computing device 112 may not be applicable to the event or to the request for data. Evidence request application 106 can determine applicability based on factors such as location, orientation, and vantage point of computing device 104 in relation to the location of the event. In one embodiment, the request for data may include metadata that helps evidence request application 106 determine whether the aggregated data is applicable. Metadata included in the request for data may include, but is not limited to, GPS coordinates of the event, the context of the user making the request, e.g., whether the requester is walking, riding in a car, or on a bicycle, an image of the requester, physical attributes of the requester, e.g., height, weight, or age, the color of the clothes the requester is wearing at the time of the event, the fact that the requester has fallen and in what direction the requester fell, samples of the requester's voice, and attributes of the requestors vehicle, e.g., make, model, year, color, license plate number of the vehicle.

A plurality of techniques known to one skilled in the art may be available to evidence request application 106 for determination of data applicability. The techniques include, but are not limited to, facial recognition, optical character recognition, deep learning algorithms, algorithms that can estimate a person's age, weight, or height, algorithms that can match objects or colors, algorithms that can estimate the direction a person or object is moving or falling, and voice recognition software.

For example, as discussed with respect to FIG. 2, evidence request application 106 on computing device 104 can determine whether data generated by a rear-view camera included in sensor(s) 108 is applicable. In the example, sensor(s) 108 also include a GPS device and a compass, and evidence request application 106 determines the location of the car via GPS coordinates and the direction the car is heading, and therefore the direction the rear-view camera is facing, via the compass. If the metadata associated with the evidence request includes the GPS coordinates of the event, then evidence request application 106 can determine whether the rear view camera was facing the event by comparing the location and direction of the camera to the location of the event, thus determining whether any images captured may be applicable. In addition, evidence request application 106 may use the focal point of the camera to determine the distance with which the camera can accurately capture an image. Evidence request application 106 can determine the distance between the camera and the event, using GPS coordinates, and if the distance is smaller than the range of the camera, then there is a higher likelihood that the evidence is applicable.

In another example, the user of participant computing device 118 is walking, and participant computing device 118 is the user's smart phone. The user of participant computing device 118 suddenly falls, and participant computing device 118 issues a request for data. Metadata included in the request for data includes a photo of the user's face and a photo of the user's current clothing. Evidence request application 106 on computing device 104 uses facial recognition software to analyze the metadata in the evidence request and determine whether any of the aggregated data includes a face that matches the face of the requestor. An image that includes the matching face may be applicable data. In addition, evidence request application 106 on computing device 104 may use color matching software to analyze the metadata in the evidence request and determine whether any of the aggregated data includes colors that match the clothing of the requestor. An image that includes the matching colors may be applicable data.

In a further example, the user of participant computing device 118 is driving, and participant computing device 118 is the user's car. Participant computing device 118 is involved in a collision, and issues a request for data. Metadata included in the request for data includes attributes of the car, such as the make, model, year, color, and license plate number. Evidence request application 106 on computing device 104 uses a similarity algorithm to determine whether any of the aggregated data includes an image of the car described by the metadata. Evidence request application 106 may also use optical character recognition to determine whether any of the aggregated data includes the license plate number of the car described by the metadata. If evidence request application 106 detects the car or the license plate in the aggregated data, then the data may be applicable.

In another embodiment, evidence request application 106 can determine whether aggregated data is applicable by assigning a normalized score for each component of the evidence. If evidence request application 106 determines the score exceeds a pre-defined threshold, then the data is applicable. For example, evidence request application 106 may assign an applicability score between zero and one for items such as time, location, and vantage point, and if the average component score is above 0.8 then the data is applicable. In a further embodiment, evidence request application 106 may transmit the applicability score to participant computing device 118, from which evidence request application 106 on participant computing device 118 can determine whether the aggregated data is applicable. In an embodiment, evidence request application 106 may determine that a portion of the aggregated data is applicable while a portion of the aggregated data is not applicable.

If evidence request application 106 determines the aggregated data is applicable ("yes" branch, decision block 406), then evidence request application 106 applies a policy to the data (step 408). In an embodiment, evidence request application 106 includes one or more policies that can be applied to the aggregated data. In one embodiment, the user may define one or more of the policies via a user interface. In another embodiment, a provider of the computing device may pre-define one or more of the policies. In a further embodiment, a provider of evidence request application 106 may pre-define one or more of the policies. In yet another embodiment, an insurance organization or a government authority may pre-define one or more of the policies. The policy includes a set of rules for how evidence request application 106 handles the aggregated data. The policy may include rules for when evidence request application 106 shares the aggregated data. For example, if evidence request application 106 determines the user of computing device 104 was speeding at the time the data was generated, then do not share the data. The policy may include rules regarding when evidence request application 106 shares the data. For example, if the data set is too large for the current network bandwidth, then send the data at a later time. The policy may include rules for when the aggregated data should be stored versus discarded. For example, if evidence request application 106 determines the data is not applicable to the event, then discard the data. The policy may include what entity receives the data. For example, evidence request application 106 may determine that some of the data should be sent to first responders while some of the data should be sent to an insurance company. In one embodiment, evidence request application 106 may prompt the user of computing device 104, via a user interface, to make a decision regarding the policy rules.

Evidence request application 106 determines whether the policy allows data transmission (decision block 410). Based on the rules included in the policy, evidence request application 106 determines whether the policy allows transmission of some or all of the aggregated data to one or more entities. If evidence request application 106 determines the policy allows data transmission ("yes" branch, decision block 410), then evidence request application 106 transmits the data (step 412).

Responsive to transmitting the data, or if evidence request application 106 determines the policy does not allow data transmission ("no" branch, decision block 410), then evidence request application 106 determines whether to store the data (decision block 414). In one embodiment, evidence request application 106 determines whether to store the aggregated data based on a policy, as described with respect to step 408. In another embodiment, evidence request application 106 determines whether to store the aggregated data based on the amount of free storage space in an associated database, such as database 110 on computing device 104.

If evidence request application 106 determines to store the data ("yes" branch, decision block 414), then evidence request application 106 stores the data (step 416). In one embodiment, evidence request application 106 stores the data in a database associated with the computing device, such as database 110 on computing device 104. In another embodiment, evidence request application 106 may store the data on a centralized server computer in a cloud network, via network 102.

If evidence request application 106 determines not to store the data ("no" branch, decision block 414), or if evidence request application 106 determines the aggregated data is not applicable ("no" branch, decision block 406), then evidence request application 106 discards the data (step 418).

In an embodiment of the present invention, the operational steps of evidence request application 106 may be performed by a server computer. For example, the server computer may detect an occurrence of an event, broadcast a request for evidence to one or more computing devices in a location of the event, and receive evidence data from the one or more computing devices. The server computer can then determine applicability of the evidence data.

Figure 5:
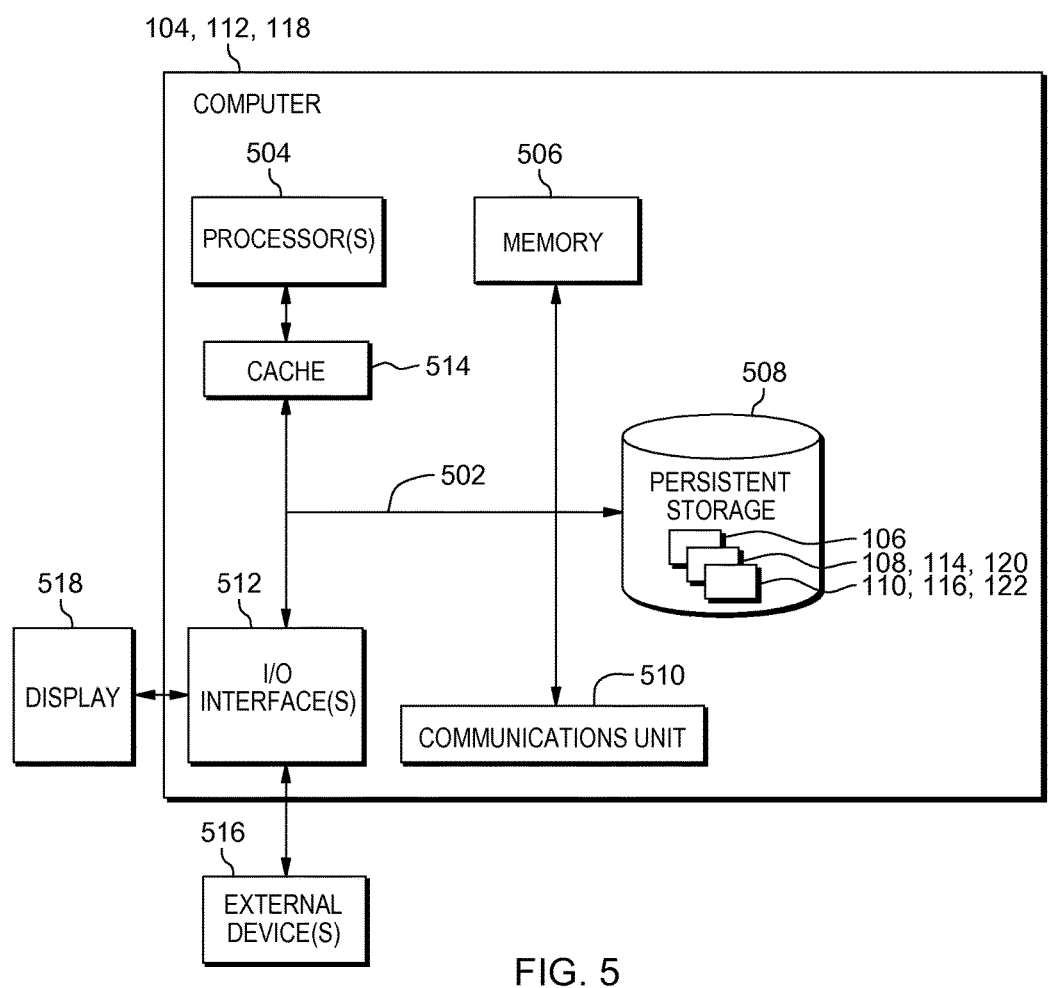
FIG. 5 depicts a block diagram of components of the computing devices executing the evidence request application within the distributed data processing environment of FIG. 1, in accordance with an embodiment of the present invention.

FIG. 5 depicts a block diagram of components of computing devices 104 and 112 and participant computing device 118 within distributed data processing environment 100 of FIG. 1, in accordance with an embodiment of the present invention. It should be appreciated that FIG. 5 provides only an illustration of one implementation and does not imply any limitations with regard to the environments in which different embodiments can be implemented. Many modifications to the depicted environment can be made.

Computing devices 104 and 112 and participant computing device 118 can each include processor(s) 504, cache 514, memory 506, persistent storage 508, communications unit 510, input/output (I/O) interface(s) 512 and communications fabric 502. Communications fabric 502 provides communications between cache 514, memory 506, persistent storage 508, communications unit 510, and input/output (I/O) interface(s) 512. Communications fabric 502 can be implemented with any architecture designed for passing data and/or control information between processors (such as microprocessors, communications and network processors, etc.), system memory, peripheral devices, and any other hardware components within a system. For example, communications fabric 502 can be implemented with one or more buses.

Memory 506 and persistent storage 508 are computer readable storage media. In this embodiment, memory 506 includes random access memory (RAM). In general, memory 506 can include any suitable volatile or non-volatile computer readable storage media. Cache 514 is a fast memory that enhances the performance of processor(s) 504 by holding recently accessed data, and data near recently accessed data, from memory 506.

Program instructions and data used to practice embodiments of the present invention, e.g., evidence request application 106, sensor(s) 108, and database 110 are stored in persistent storage 508 of computing device 104 for execution and/or access by one or more of the respective processor(s) 504 of computing device 104 via memory 506. Program instructions and data used to practice embodiments of the present invention, e.g., evidence request application 106, sensor(s) 114, and database 116 are stored in persistent storage 508 of computing device 112 for execution and/or access by one or more of the respective processor(s) 504 of computing device 112 via memory 506. Program instructions and data used to practice embodiments of the present invention, e.g., evidence request application 106, sensor(s) 120, and database 122 are stored in persistent storage 508 of participant computing device 118 for execution and/or access by one or more of the respective processor(s) 504 of participant computing device 118 via memory 506. In this embodiment, persistent storage 508 includes a magnetic hard disk drive. Alternatively, or in addition to a magnetic hard disk drive, persistent storage 508 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 508 may also be removable. For example, a removable hard drive may be used for persistent storage 508. Other examples include optical and magnetic disks, thumb drives, and smart cards that are inserted into a drive for transfer onto another computer readable storage medium that is also part of persistent storage 508.

Communications unit 510, in these examples, provides for communications with other data processing systems or devices. In these examples, communications unit 510 includes one or more network interface cards. Communications unit 510 may provide communications through the use of either or both physical and wireless communications links. Evidence request application 106, sensor(s) 108, and database 110 may be downloaded to persistent storage 508 of computing device 104 through communications unit 510. Evidence request application 106, sensor(s) 114, and database 116 may be downloaded to persistent storage 508 of computing device 112 through communications unit 510. Evidence request application 106, sensor(s) 120, and database 122 may be downloaded to persistent storage 508 of participant computing device 118 through communications unit 510.

I/O interface(s) 512 allows for input and output of data with other devices that may be connected to computing device 104, computing device 112, and participant computing device 118. For example, I/O interface(s) 512 may provide a connection to external device(s) 516 such as a keyboard, a keypad, a touch screen, a microphone, a digital camera, and/or some other suitable input device. External device(s) 516 can also include portable computer readable storage media such as, for example, thumb drives, portable optical or magnetic disks, and memory cards. Software and data used to practice embodiments of the present invention, e.g., evidence request application 106, sensor(s) 108, and database 110 on computing device 104, can be stored on such portable computer readable storage media and can be loaded onto persistent storage 508 via I/O interface(s) 512. I/O interface(s) 512 also connect to a display 518. Software and data used to practice embodiments of the present invention, e.g., evidence request application 106, sensor(s) 114, and database 116 on computing device 112, can be stored on such portable computer readable storage media and can be loaded onto persistent storage 508 via I/O interface(s) 512. I/O interface(s) 512 also connect to a display 518. Software and data used to practice embodiments of the present invention, e.g., evidence request application 106, sensor(s) 120, and database 122 on participant computing device 118, can be stored on such portable computer readable storage media and can be loaded onto persistent storage 508 via I/O interface(s) 512. I/O interface(s) 512 also connect to a display 518.

Display 518 provides a mechanism to display data to a user and may be, for example, a computer monitor. Display 518 can also function as a touchscreen, such as a display of a tablet computer.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for cooperative evidence gathering, the method comprising:
    receiving, by a first computing device, a request for data corresponding to an event, wherein a second computing device detecting the event initiates the request for data;
    triggering, by the first computing device, one or more sensors to activate, the one or more sensors associated with one or more computing devices within a proximity of a location of the event;
    aggregating, by the first computing device, data from the one or more sensors;
    analyzing, by the first computing device, metadata associated with the request for data, wherein the metadata associated with the request for data includes one or more attributes of the event, and wherein analyzing metadata associated with the request for data includes utilizing, by the first computing device, at least one of: facial recognition software, optical character recognition software, an algorithm that can estimate one or more physical characteristics of a person, an algorithm that can match one or more colors between one or more images, an algorithm that can estimate a direction a person or object is moving, or voice recognition software;
    determining, by the first computing device, whether the aggregated data corresponds to the metadata associated with the request for data;
    determining, by the first computing device, whether at least a portion of the aggregated data is applicable to the event, based, at least in part, on the metadata associated with the request for data and on one or more of: a location determined by global positioning system coordinates, an orientation, a vantage point, and a focal point of the one or more sensors in relation to a location of the event;
    responsive to determining at least a portion of the aggregated data is applicable to the event, applying, by the first computing device, one or more rules corresponding to the aggregated data;
    based, at least in part, on the applied one or more rules, determining, by the first computing device, to whom to transmit the applicable data; and
    transmitting, by the first computing device, the data to a computer system of an insurance company and the second computing device.

2. The method of claim 1, wherein determining whether at least a portion of the aggregated data is applicable to the event further comprises:
    assigning, by the first computing device, a normalized score to the aggregated data; and
    determining, by the first computing device, whether the normalized score exceeds a pre-defined threshold.

3. The method of claim 1, further comprising, transmitting, by the first computing device, the data to at least one of: a first responder or a health care provider.

4. The method of claim 1, further comprising, based, at least in part, on the applied one or more rules, determining, by the first computing device, whether to store the applicable data.

5. The method of claim 1, wherein the request for data corresponding to the event includes one or more of: a question about the event, an entity to which to send the data, information about the event, a location of the event, a time the event occurred, a geo-temporal point of interest, a description of a party involved in the event, or sample evidence.

6. A computer program product for cooperative evidence gathering, the computer program product comprising:
    one or more computer readable storage device and program instructions stored on the one or more computer readable storage device, the stored program instructions comprising:
    program instructions to receive a request for data corresponding to an event, wherein a second computing device detecting the event initiates the request for data;
    program instructions to trigger one or more sensors to activate, the one or more sensors associated with one or more computing devices within a proximity of a location of the event;
    program instructions to aggregate data from the one or more sensors;
    program instructions to analyze metadata associated with the request for data, wherein the metadata associated with the request for data includes one or more attributes of the event, and wherein analyzing metadata associated with the request for data includes program instructions to utilize at least one of: facial recognition software, optical character recognition software, an algorithm that can estimate one or more physical characteristics of a person, an algorithm that can match one or more colors between one or more images, an algorithm that can estimate a direction a person or object is moving, or voice recognition software;
    program instructions to determine whether the aggregated data corresponds to the metadata associated with the request for data;
    program instructions to determine whether at least a portion of the aggregated data is applicable to the event, based, at least in part, on the metadata associated with the request for data and on one or more of: a location determined by global positioning system coordinates, an orientation, a vantage point, and a focal point of the one or more sensors in relation to a location of the event;
    responsive to determining at least a portion of the aggregated data is applicable to the event, program instructions to apply one or more rules corresponding to the aggregated data;
    based, at least in part, on the applied one or more rules, program instructions to determine to whom to transmit the applicable data; and
    program instructions to transmit the data to a computer system of an insurance company and the second computing device.

7. The computer program product of claim 6, the stored program instructions further comprising, program instructions to transmit the data to at least one of: a first responder or a health care provider.

8. The computer program product of claim 6, the stored program instructions further comprising, based, at least in part, on the applied one or more rules, program instructions to determine whether to store the applicable data.

9. A computer system for cooperative evidence gathering, the computer system comprising:
 one or more computer processors;
 one or more computer readable storage device;
 program instructions stored on the one or more computer readable storage device for execution by at least one of the one or more computer processors, the stored program instructions comprising:
 program instructions to receive a request for data corresponding to an event, wherein a second computing device detecting the event initiates the request for data;
 program instructions to trigger one or more sensors to activate, the one or more sensors associated with one or more computing devices within a proximity of a location of the event;
 program instructions to aggregate data from the one or more sensors;
 program instructions to analyze metadata associated with the request for data, wherein the metadata associated with the request for data includes one or more attributes of the event, and wherein analyzing metadata associated with the request for data includes program instructions to utilize at least one of: facial recognition software, optical character recognition software, an algorithm that can estimate one or more physical characteristics of a person, an algorithm that can match one or more colors between one or more images, an algorithm that can estimate a direction a person or object is moving, or voice recognition software;
 program instructions to determine whether the aggregated data corresponds to the metadata associated with the request for data;
 program instructions to determine whether at least a portion of the aggregated data is applicable to the event, based, at least in part, on the metadata associated with the request for data and on one or more of: a location determined by global positioning system coordinates, an orientation, a vantage point, and a focal point of the one or more sensors in relation to a location of the event;
 responsive to determining at least a portion of the aggregated data is applicable to the event, program instructions to apply one or more rules corresponding to the aggregated data;
 based, at least in part, on the applied one or more rules, program instructions to determine to whom to transmit the applicable data; and
 program instructions to transmit the data to a computer system of an insurance company and the second computing device.

10. The computer system of claim 9, the stored program instructions further comprising, program instructions to transmit the data to at least one of: a first responder or a health care provider.

\* \* \* \* \*